(12) United States Patent
Kinugasa et al.

(10) Patent No.: US 7,414,038 B2
(45) Date of Patent: Aug. 19, 2008

(54) EMBOLIC MATERIALS

(75) Inventors: Kazushi Kinugasa, Okayama (JP); Shinya Mandai, Kagawa (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 757 days.

(21) Appl. No.: 10/148,971

(22) PCT Filed: Oct. 5, 2001

(86) PCT No.: PCT/JP01/08818

§ 371 (c)(1),
(2), (4) Date: Jun. 10, 2002

(87) PCT Pub. No.: WO02/30485

PCT Pub. Date: Apr. 18, 2002

(65) Prior Publication Data

US 2002/0183764 A1 Dec. 5, 2002

(30) Foreign Application Priority Data

Oct. 10, 2000 (JP) .............................. 2000-309605

(51) Int. Cl.
*A61K 31/719* (2006.01)
*A61L 24/08* (2006.01)
*A61L 31/04* (2006.01)
*A61K 31/717* (2006.01)
*A61K 31/718* (2006.01)
*A61K 31/721* (2006.01)

(52) U.S. Cl. ................. 514/54; 536/123.12; 424/9.322; 424/423

(58) Field of Classification Search ............. 536/63–69, 536/123.12; 514/57, 54; 424/9.322, 9.32, 424/9.34, 423
See application file for complete search history.

(56) References Cited

U.S. PATENT DOCUMENTS

| 4,029,886 | A | * | 6/1977 | Nakashio et al. ............ 536/120 |
| 5,202,352 | A | * | 4/1993 | Okada et al. ................ 514/475 |
| 5,580,568 | A | * | 12/1996 | Greff et al. .................. 424/423 |
| 5,624,685 | A | | 4/1997 | Takahashi et al. |
| 5,702,361 | A | * | 12/1997 | Evans et al. ................. 604/508 |
| 5,856,468 | A | * | 1/1999 | Shuto et al. .................. 536/64 |
| 5,928,613 | A | * | 7/1999 | Yamashita .................. 422/188 |
| 5,990,304 | A | * | 11/1999 | Kiyose et al. ................. 536/69 |
| 7,122,660 | B1 | * | 10/2006 | Nakanishi et al. ............ 536/69 |

FOREIGN PATENT DOCUMENTS

| JP | 57-141401 A | 9/1982 |
| JP | 6-107549 A | 4/1994 |
| JP | 11-76249 A | 3/1999 |
| WO | WO 94/06503 A1 | 3/1994 |
| WO | WO 97/04813 A | 2/1997 |
| WO | WO 00/01342 A1 | 1/2000 |

OTHER PUBLICATIONS

Hirotsune, N. et al "Combined use of cellulose acetate polymer ..." Acta Med. Okayama (2000) vol. 54, No. 4, pp. 153-164.*
Matsumaru, Y. et al "Embolic materials for endovascular treatment ..." J. Biomater. Sci. Polym. Edn. (1997) vol. 8, No. 7, pp. 555-569.*
Roy Wissler, ed. Methods in Carbohydrate Chemistry, Academic Press, vol. 3, pp. 201-203, 1963.
Shu Kanbara, ed. "Kobunshi-Jikken-Gaku (Experimental Study on Macromolecules)", published by Kyoritsu Shuppan Publisher, vol. 8, pp. 301-305, 1984.
Kenji Kamide et al, "The Viscometric and Light-Scattering Determination of Dilute Solution Properties of Cellulose Diacetate", Polymer LJournal, vol. 11, No. 4, pp. 285-298, 1979.

* cited by examiner

*Primary Examiner*—Leigh C Maier
(74) *Attorney, Agent, or Firm*—Browdy and Neimark

(57) ABSTRACT

The object of the present invention is to provide an embolizing material which is easily handleable and stable in quality and is solved by providing an embolizing material comprising an ester derivative of a polysaccharide having a weight-average molecular weight of 10,000-500,000 daltons and an average substitution degree of acyl group of over two; an embolizing agent for arteriovenous aneurysm, which comprises the embolizing material and an appropriate physiologically acceptable water-soluble organic acid; and a method of producing an embolizing agent, which comprises a step of dissolving the embolizing material in an appropriate physiologically acceptable water-soluble organic solvent.

6 Claims, No Drawings

EMBOLIC MATERIALS

REFERENCE TO RELATED APPLICATIONS

The present application is the national stage under 35 U.S.C. 371 of international application PCT/JP01/08818, filed Oct. 10, 2000, which designated the United States, and which application was not published in the English language.

FIELD OF THE INVENTION

The present invention relates to an embolizing material which is effective to arteriovenous aneurysm, more particularly, to an embolizing material comprising an ester derivative of a polysaccharide, and uses thereof.

BACKGROUND OF THE INVENTION

Arteries and veins may locally, abnormally flutter and form arteriovenous aneurysms due to injury, vascular sclerosis, high blood pressure, bacterial infection, disorder of venous valves, malformation, etc. Among these arteriovenous aneurysms, those which have bosselated walls of intracranial arteries such as internal carotid arteries, anterior cerebral/anterior communicating arteries, middle cerebral arteries, and vertebral basilar arteries are called cerebral aneurysm that induces subarachnoid hemorrhage when ruptured. It is said that about 10% of stroke is subarachnoid hemorrhage and reported that the appearance of patients with the disease is as many as 30,000 a year in Japan. It is also said that 80% or more of such patients will usually die after repeating the rupture of cerebral aneurism. Therefore, both the finding of cerebral aneurism at an earlier stage and the embolization of affected parts must be the best way to prevent subarachnoid hemorrhage.

As conventional methods for embolizing cerebral aneurysm, direct surgeries such as clipping and ligation of parent arteries of aneurysm have been generally used, but they have been frequently replaced with intravascular surgeries that embolize cerebral aneurysm by inserting platinum coils into the cavity of cerebral aneurysm in these days. However, the method using platinum coils has the drawbacks that the installation of materials such as blebs with a complicated shape might possibly fail the complete embolization of aneurysm, the installed coil might cause recirculation of blood when compressed within the aneurysm, and that thrombus formed interstitially in the aneurysm might move into a normal brain part to cause fatal cerebral infarction.

As a method of overcoming the above drawbacks of conventional methods, the present inventors proposed in Japanese Patent Kokai No. 107,549/94, etc., a liquid embolizing material for embolizing aneurysm which is used for embolization in such a manner of injecting into the cavity of aneurysm a non-water-soluble macromolecule such as cellulose acetate dissolved in a water-soluble organic solvent, dispersing the water-soluble organic solvent throughout the cavity, and precipitating and solidifying the macromolecule therein to embolize the aneurysm. Since the above embolizing material also exerts a remarkable effect on aneurysm having a complicated shape of cavity, it has been valued as a theoretically advantageous one. The macromolecule used, for example, in Japanese Patent Kokai No. 107,549/94, however, there still remains a problem to be solved in preparing a relatively high quality, stabilized embolizing agent in a satisfactorily yield because the macromolecule has inconsistent solubility and viscosity in water-soluble organic solvents such as dimethylsulfoxide (may be abbreviated as "DMSO", hereinafter).

SUMMARY OF THE INVENTION

In view of the aforesaid background, the object of the present invention provides an embolizing material used in preparing embolizing agents for arteriovenous aneurysm, which have easy handleability and stable quality and which are produced in a relatively high yield; and uses thereof.

Among a variety of macromolecules having different origins, properties, and chemical structures, the present inventors focused on derivatives of polysaccharides as physiologically-easily-acceptable materials, and energetically studied and screened for weight-average molecular weights and average substitution degrees of substituents. As a result, they found the desired ester derivatives of polysaccharides having a weight-average molecular weight of 10,000-500,000 daltons and an average substitution degree of acyl group of over two. The ester derivatives do not substantially dissolve in blood but have both relatively high solubility in water-soluble organic solvents and an easily controllable precipitation and solidification rate in blood. Based on these, the present inventors found that the above ester derivatives facilitate the preparation of embolizing agents for arteriovenous aneurysm, which are easily handleable and stable in quality.

The present invention solves one of the above objects by providing an embolizing material which comprises an ester derivative of a polysaccharide having a weight-average molecular weight of 10,000-500,000 daltons and an average substitution degree of acyl group of over two.

Further, the present invention solves another one of the above objects by providing an embolizing agent for arteriovenous aneurysm, which comprises the embolizing material and an appropriate physiologically acceptable water-soluble organic solvent.

In addition, the present invention solves further one of the above objects by providing a method of preparing an embolizing agent for arteriovenous aneurysm, which comprises a step of dissolving the above embolizing material in a physiologically acceptable water-soluble organic solvent.

DETAILED DESCRIPTION OF THE INVENTION

As described above, the present invention relates to an embolizing material comprising an ester derivative of a polysaccharide having a weight-average molecular weight of 10,000-500,000 daltons and an average substitution degree of acyl group of over two. The term "a polysaccharide(s)" as referred to as in the present invention means a macromolecule(s) in general which has a repeating unit of a saccharide such as glucose, galactose, mannose, rhamnose, and xylulose. Among these polysaccharides, simple polysaccharides such as starches, amyloses, amylopectins, celluloses, pullulans, elsinans, and dextrans, which have a repeating unit of glucose and do not substantially induce undesirable side effect on blood cells, tissues, and blood components, can be preferably used because, in use, the embolizing material of the present invention is in itself directed to intravascularly inject into living bodies for contacting with blood cells and tissues.

Thus, the term "ester derivatives of polysaccharides" as referred to as in the present invention includes those in which hydrogen atoms in the hydroxy groups of the polysaccharides are substituted with acyl groups. Examples of such acyl groups include alkyl carbonyl groups such as formyl, acetyl, propionyl, butyl, isobutyl, valeryl, isovaleryl, pivaloyl, hexanoyl, octanoyl, acryloyl, metaacryloyl, pyruvoyl, oxalo, methooxalyl, and ethoxalyl groups; cycloalkylcarbonyl groups such as cyclopropylcarbonyl, cyclobutylcarbonyl, cyclopentylcarbonyl, and cyclohexylcarbonyl groups; and aryl carbonyl groups such as benzoyl, o-toluoyl, m-toluoyl, p-toluoyl, and cinnamoyl groups, which are appropriately selected depending on use and the types of polysaccharides used. Varied depending on the types of polysaccharides and the types of and the occurring parts of arteriovenous aneurysm to be embolized, it is preferably be selected physiologically acceptable polysaccharides as much as possible because, as described above, the embolizing material of the present invention is in itself directed to intravascularly inject into living bodies for contacting with blood cells and tissues. In view of this, the most preferable acyl groups are alkylcarbonyl groups such as acetyl and propionyl groups; and among these, acetyl group is preferably used when simple saccharides such as cellulose are used as polysaccharides.

In the present invention, as described above, to provide an embolizing agent for arteriovenous aneurysm which is easily handleable and stable in quality, among the above ester derivatives, those which have a weight-average molecular weight of 10,000-500,000 daltons, preferably, 30,000-300,000 daltons, and more preferably, those which have the above weight-average molecular weights and ratios ((weight-average molecular weight)/(number average molecular weight)) of below two, preferably, a ratio in the range of 1.1-1.5, and those which have an average substitution degree of acyl group of over two, preferably, 2.5 or higher can be preferably selected. The reason of defining the weight-average molecular weight as such is that ester derivatives of polysaccharides with a lower weight-average molecular weight than the above lower limit have improved solubility and free-flowing ability in water-soluble organic solvents but they do not become promptly and rigidly precipitate and solidify within the cavity of arteriovenous aneurysm and fail to completely embolize aneurysm, while those with a higher weight-average molecular weight than the above upper limit promptly precipitate and solidify within the cavity of arteriovenous aneurysm but they reduce their solubility and free-flowing ability in water-soluble organic solvents and lose their handleability. Among these ester derivatives, since those which have a ratio ((weight-average molecular weight)/(number average molecular weight)) of below two are composed of molecules having a similar polymerization degree and substitution degree, they have advantages of being easily handled when prepared into solutions of water-soluble organic solvents and readily controlled their precipitation and solidification in blood.

The reason of defining the average substitution degree of acyl group to a level of over two is as follows: When the substitution degree of below two, the resulting ester derivatives of polysaccharides have lower solubility in water-soluble organic solvents, lesser handleability, and lower processibility; and depending on polysaccharides used, the ester derivatives easily dissolve in blood and may case undesirable results in embolizing arteriovenous aneurysm. In the case of ester derivatives of simple polysaccharides having a repeating unit of glucose, they increase their solubility in water-soluble organic solvents as the increase of average substitution degree but decrease their viscosity in a solution form. Particularly, ester derivatives with an average substitution degree of acyl group of 2.5 or higher, even though they have a relatively high weight-average molecular weight, are preparable by dissolving in water-soluble organic solvents such as DMSO into solutions, having adequate viscosity and flexibility, to facilitate their injection into the cavity of arteriovenous aneurysm by using intracatheters when in embolizing surgery. In general, ester derivatives with a higher weight-average molecular weight have a higher precipitation and solidification rate in blood and form a more rigid solid mass. By adjusting the average substitution degree of acyl group to a level of 2.5 or over, even ester derivatives having a relatively high weight-average molecular weight, which could not have been easily injected into the cavity of arteriovenous aneurysm because of their low solubility in water-soluble organic solvents, can be easily injected into the cavity. The average-weight molecular weight, the number average molecular weight, and the average substitution degree can be determined by or in accordance with conventional methods. For example, the weight-average molecular weight and the number average molecular weight can be determined by the method disclosed by Kenji Kamide et al., in *Polymer Journal*, Vol. 11, No. 4, pp. 285-298 (1979), and the average substitution degree can be determined by the method disclosed in *Methods in Carbohydrate Chemistry*, Vol. 3, pp. 201-203 (1963), edited by Roy L. Wissler, published by Academic Press.

The ester derivatives of polysaccharides as mentioned above can be prepared by various methods. In the case of using cellulose as a polysaccharide and of introducing alkylcarbonyl group into the polysaccharide, for example, the methods using as an acylating agent acid anhydrides, acid halides, ketenes, and the like, as disclosed, for example, in *Methods in Carbohydrate Chemistry*, Vol. 3, pp. 193-198 (1963), edited by Roy L. Wissler, published by Academic Press, and in "*Kobunshi-Jikken-Gaku (Experimental Study on Macromolecules)*", Vol. 8, pp. 301-305 (1984), edited by Shu Kanbara, published by Kyoritsu Shuppan Publisher. The desired ester derivatives usable in the present invention can be prepared in accordance with the above methods even when either polysaccharides other than cellulose are used, or cycloalkylcarbonyl or arylcarbonyl group is introduced into polysaccharides. In the case of commercialized ester derivatives of polysaccharides having the desired weight-average molecular weight and average substitution degree are available, they can be used intact. Independently of using such commercialized products or those prepared by the above methods, when they do not have a weight-average molecular weight being in the desired range, they are, for example, subjected to conventional methods such as differential chromatography and sedimentation to collect fractions with the desired weight-average molecular weight; or when the above both products have a lower average substitution degree than the above desired range, they can be prepared into ester derivatives of polysaccharides having the desired average substitution degree by applying re-esterification methods as described in the aforesaid publications. To prepare ester derivatives of polysaccharides having a ratio ((weight-average molecular weight)/(number average molecular weight)) of below two, the liquid fractionation method as disclosed, for example, by Kenji Kamide, in "*Polymer Journal*", Vol. 11, No. 4, pp. 285-298 (1979), can be applied to those having a ratio ((weight-average molecular weight)/(number average molecular weight)) of over two. Prior to use, the resulting ester derivatives can be purified in accordance with conventional methods, which are commonly used for purifying medical macromolecules, such as extraction, dialysis, dissolution, concentration, filtration, sedimentation, decantation, fractionation, and washing/cleansing, which are usable in combination, if necessary.

These ester derivatives of polysaccharides are advantageously useful as embolizing materials for preparing embolizing agents for arteriovenous aneurysm. The embolizing agent for arteriovenous aneurysm of the present invention comprises the above-mentioned ester derivative(s) of polysaccharide(s) and an appropriate physiologically acceptable water-soluble organic solvent(s), and optionally a contrast medium for angiography can be incorporated into the embolizing agent within the range that does not affect the object of the present invention. The term "water-soluble organic solvents" as referred to as in the present invention means organic solvents in general which dissolve the ester derivatives of polysaccharides at temperatures at which the embolizing agent of the present invention is used, for example, temperatures of around 37° C. as the body temperatures of living bodies in general, and which disperse into the blood without substantially affecting the bodies. Examples of such organic solvents are ethanol, propanol, isopropanol, acetone, N,N-dimethylacetamide, diethylether, ethyl methyl ketone, isobutyl methyl ketone, DMSO, and mixtures thereof. Among these solvents, DMSO is most preferably used in practicing the present invention because it well dissolves the ester derivatives of polysaccharides used in the present invention and has a relatively high safeness to living bodies.

The contrast media for angiography used in the present invention are those for fluororoentgenographically, macroscopically observing the embolus condition of arteriovenous aneurysm during and after surgery, and any one of those conventionally used in angiography can be used without specific restriction. Examples of such agents are iodides including amidotrizoic acid, sodium amidotrizoate, iotalamic acid, metrizoic acid, iodamide, ioxaglic acid, iopamidol, iohexol, and iotrolan; bismuth compounds such as dibismuth trioxide; and metal powders such as tantalum powder, which are optionally used in an appropriate combination.

The embolizing agent for arteriovenous aneurysm of the present invention is usually prepared through the steps of adding appropriate amounts of ester derivatives of polysaccharides to the above-mentioned water-soluble organic solvents, and optionally dissolving under heating and stirring conditions the derivatives in the solvents in a final concentration of at least one percent by weight, preferably, 3 to 10% by weight. If necessary, after filtration, the resulting solutions of the ester derivatives are distributed into appropriate vessels such as amples and vials, and then sterilized, followed by sealing the vessels. The embolizing agent for arteriovenous aneurysm of the present invention should have appropriate viscosity and free-flowing ability at ambient temperature because, in use, it is injected into the cavity of arteriovenous aneurysm through minute tubes such as intracatheters. When dissolved in the above water-soluble organic solvents within the above range of concentration, the ester derivatives having a specific weight-average molecular weight and average substitution degree can be prepared into solutions with a viscosity of below 1,000 centipoises (cps) at 20° C., preferably, about 50 to about 500 cps. Since these solutions have appropriate viscosity, free-flowing ability, and easy handleability, they are preferably used in embolizing surgery using intracatheters.

Now explaining the use of the embolizing agent for arteriovenous aneurysm of the present invention, the embolizing agent can be applied to arteriovenous aneurysm similarly as in conventional liquid embolizing agents. In relation to the use of the embolizing agent of the present invention, as an example, the embolizing surgery using intracatheters will be explained: All the surgery techniques are applied to patients, who are, in principle, locally anesthetized and vigilance, using intrafluoroscopes equipped with a road-map function. First, place a 6-fr sheath in a patient's either thigh; next, insert through the sheath a 6-fr intracatheter into the patient's artery; then, inject a contrast medium for angiography into the artery via the intracatheter; and finally, fluoroscope the patient's intracranial arteries. Based on the fluoroscopic data, the following are determined: The affected part, size, and shape of aneurysm, as well as the route to the aneurysm, the positional relationship between a pedicel of the aneurysm and its parent aneurysm, and the degree of collateral circulation. Thereafter, a micro-catheter is inserted into and passed through the intracatheter until the micro-catheter's top reaches the deepest part of the cavity of the aneurysm. In this case, when the micro-catheter could not be inserted into the aneurysm, either the shape of the top of the micro-catheter is deformed or a guide wire is used in combination. When the aneurysm is an anterior aneurysm of Willis arterial circle, prior to the injection of the embolizing agent, a contrast medium is preliminarily injected into the aneurysm through the micro-catheter placed in the cavity of the aneurysm while pressing carotid artery so as not to flow out the embolizing agent far apart from the aneurysm, followed by confirming the staying of the contrast medium within the cavity. In the case of aneurysm occurred in vertebral basilar artery, another intracatheter is inserted into the patient's another thigh and a micro-balloon is inserted into a parent vain through the another intracatheter to interrupt the blood flow.

Then, a fresh preparation of a similar water-soluble organic solvent as used in the embolizing agent is injected for washing into the intracatheter, and then the embolizing agent is gradually injected into the intracatheter under fluoroscopic observation. In parallel, a contrast medium for angiography is injected through the another intracatheter inserted into the patient's another thigh to fluoroscopically confirm the progress of embolization. When injected into the cavity of arteriovenous aneurysm, the water-soluble organic solvents in the embolizing agent for arteriovenous aneurysm of the present invention instantly disperses in blood, and then the ester derivatives of polysaccharides form a clot-like mass in compliance with the shape of the cavity of the arteriovenous aneurysm, gradually precipitate and solidify from the surface to the central part of the arteriovenous aneurysm, resulting in forming a water-insoluble solid mass. In this case, the clot-like mass initiates to precipitate and solidify from the surface of the arteriovenous aneurysm as soon as contacting with blood, and the internal part of the mass solidifies within a few minutes, usually, within about two minutes. After solidification of the ester derivatives, the blood circulation is restarted and the presence or the absence of a pedicel of aneurysm is fluoroscopically observed. When the pedicel is remained, a similar surgical technique is repeated to completely embolize the cavity of arteriovenous aneurysm.

A more preferred embodiment using the embolizing agent for arteriovenous aneurysm of the present invention is the embolizing surgery which uses the embolizing agent in combination or sequentially, for example, with coils for embolizing arteriovenous aneurysm such as coils made of titanium, platinum, gold, or alloys thereof, or synthetic resins. With the method, the coils act as a "frame" within the cavity of arteriovenous aneurysm and the ester derivatives of polysaccharides precipitate and solidify in and around the coils to form a rigid solid mass that could not be easily attained by either of them alone. Thus, according to the method, even when applied to arteriovenous aneurysm with a relatively large volume of or a complicated shape of cavity, the arteriovenous aneurysm can be perfectly and semi-permanently embolized without remaining any pedicel with only a single surgery, and this distinctively increases and widens the effectiveness and the range of applicability of embolizing surgery for arteriovenous aneurysm by vascular surgeries. The combination use of the embolizing agent of the present invention and a conventional coil for embolizing arteriovenous aneurysm allows the coil to embolize the cavity of arteriovenous aneurysm to some extent, and substantially prevents the embolizing agent from flowing out of the cavity when the agent is injected into the cavity. Accordingly, depending on the affected part, size, shape or the like of arteriovenous aneurysm to be treated, the concentration and/or the molecular weight of the ester derivatives to be incorporated into the embolizing agent are set to a slightly lower level within the aforesaid ranges to uniformly and completely embolize the cavity of arteriovenous aneurysm.

Applicable arteriovenous aneurysms, which can be treated with the embolizing agent for arteriovenous aneurysm according to the present invention, include aneurysms and varices in general occurring in living bodies, for example, aneurysms in general such as cerebral-, endoceliac-, hepatic-, arteria lienalis-, arteria renalis-, and peripheral-aneurysms in a saccular or spindle form, which are induced intracranially, viscerally or peripherally by some factors such as arteriosclerosis, microbial infections, inflammatories, and congenital features; and varices in general occurring in esophageal venous plexuses, rectal venous plexuses, paraumbilical veins, inferior limbs, pudenda, spermatic cords, etc., which are induced by the increase of venous pressure, the depression of venous wall tolerance, venous sclerosis, and the disorder of venous valves. Also, the embolizing agent very effectively embolizes intracranial arteriovenous malformation. In addition to the above medical uses, the embolizing material of the present invention has a variety of uses as those which need the embolization of a relatively minute affected part, for example, hemostatics in medical field, hemostatic agents for intravascularly blocking the blood flow in arteries and veins in medical needs; and reinforcing agents and fillers for cloths, papers, membranes, films, and sheets in the fields of clothes, paper-making, and chemicals.

The preferred embodiments according to the present invention will be described with reference to the following examples, hereinafter:

EXAMPLE 1

Embolizing Material

Twenty-five grams of cellulose acetate, having a weight-average molecular weight of 50,000 daltons and an average substitution degree of acetyl group of 1.75, were placed in a reaction vessel, dried at 110° C. for two hours, and mixed with 500 ml of a mixture solution of acetic acid and acetic anhydride (=9:1 by volume), followed by stirring the resulting mixture at ambient temperature overnight. Thereafter, 11 ml of a mixture solution of acetic acid and perchloric acid (=10:1 by volume) were added to the reaction vessel, and the mixture was stirred at a high speed for 30 min, followed by allowing the reaction mixture to precipitate according to a usual manner. The precipitate was collected, and then fractionated according to the sequential solution fractionation (SSF) method as reported by Kenji Kamide in "Polymer Journal", Vol. 11, No. 4, pp. 285-298 (1979), followed by collecting a fraction having a similar weight-average molecular weight to that of the material. Thereafter, the fraction was concentrated, precipitated, filtered, washed, and pulverized to obtain 10 g of a powdered ester derivative of cellulose, having a weight-average molecular weight of 50,000 daltons, a ratio of weight-average molecular weight to number-average molecular weight of 1.3, and an average substitution degree of acetyl group of 2.9.

Using a portion of the powder thus obtained, the solubility was determined in a usual manner and revealed that it had a solubility of over 10 mg/ml in DMSO at 20° C., and was substantially insoluble in physiological saline. As a comparison, an ester derivative of cellulose, having a weight-average molecular weight of 50,000 daltons, a ratio of weight-average molecular weight to a number-average molecular weight of 2.3, and an average substitution degree of acetyl group of 1.75, was similarly tested as above, revealing that it was substantially insoluble in physiological saline but was significantly lower in solubility in DMSO at 20° C. than that of the above ester derivative in this example. A portion of an unfractionated ester derivative in the above preparation step was sampled and tested similarly as above, revealing that it had significantly lower solubility in DMSO than that of the fractionated specimen and had a rather unfavorable handleability when dissolved.

The ester derivative in this example, having a higher solubility in water-soluble organic solvents such as DMSO and satisfactory handleability and stability in quality, will be quite advantageously used as an embolizing material for embolizing arteriovenous aneurysm, etc.

EXAMPLE 2

Embolizing Material

Five grams of pullulan, having a weight-average molecular weight of 85,000 daltons and a ratio of weight-average molecular weight to number-average molecular weight of 1.5, which had been prepared by the method disclosed in Japanese Patent Kokai No. 141,401/82 applied for by the same applicant as the present invention, were placed in a reaction vessel and admixed with 13 g of acetic anhydride and 30 g of pyridine, and the mixture was reacted at 100° C. for two hours. Thereafter, the reaction mixture was precipitated in a usual manner, filtered, washed, and pulverized to obtain four grams of a powdered ester derivative of pullulan, having a similar weight-average molecular weight to that of the material and a ratio of weight-average molecular weight to number-average molecular weight of 2.7.

Using a portion of the powder thus obtained, it was determined for solubility in a usual manner and revealed that it had a solubility of over 10 mg/ml in DMSO at 20° C. and was substantially insoluble in physiological saline. As a comparison, an ester derivative of pullulan, having a weight-average molecular weight of 85,000 daltons, a ratio of weight-average molecular weight to a number-average molecular weight of 2.1, and an average substitution degree of acetyl group of 0.95, was similarly tested as above and revealed that, unlike the product in this example, it was substantially soluble in physiological saline and was significantly low in solubility in DMSO at 20° C.

The ester derivative obtained in this example, having a higher solubility in water-soluble organic solvents such as DMSO and satisfactory handleability and stability in quality, will be quite advantageously used as an embolizing material for embolizing arteriovenous aneurysm, etc.

EXAMPLE 3

Embolizing Agent

An adequate amount of DMSO was placed in a glass vessel, admixed with 12.5 g of an ester derivative prepared by the method in Example 1 or 2, and stirred while heating until the ester derivative completely dissolved, followed by the addition of DMSO to give a total volume of 150 ml. Thereafter, using a glass syringe equipped with a filtration membrane and an aspirating needle, three milliliter aliquots of the resulting solution were distributed while heating to 5-ml brown-colored amples, and autoclaved at 115° C. for 30 min, followed by sealing the amples to obtain two types of embolizing agents.

One ample for each of the embolizing agents obtained in this example was unsealed, and the content in each ample was inhaled into a syringe and added drop by drop to physiological saline kept at 37° C., resulting in an observation of their respective instant precipitation and solidification in a spherical manner. For a comparison, using the following controls, they were observed for dynamics of dropping into physiological saline; an ester derivative of cellulose, as control 1, having a weight-average molecular weight of 50,000 daltons, a ratio of weight-average molecular weight to number-average molecular weight of 2.3, and an average substitution degree of acetyl group of 1.75; and another ester derivative of cellulose, as control 2, having a weight-average molecular weight of 5,000 daltons, a ratio of weight-average molecular weight to number-average molecular weight of 1.3, and an average substitution degree of acetyl group of 2.9, both of which had been prepared similarly as the ester derivative in this example except for appropriately lowering the concentration of the former ester derivative with a lower solubility in DMSO. As a result, control 1 precipitated and solidified similarly as the embolizing agent of the present invention, however, it had inferior handleability in preparing an embolizing agent because of its relatively low solubility in DMSO. While control 2 had a similar solubility to that of the embolizing agent of the present invention, but had a significantly lower precipitation and solidification rate in physiological saline. Upon the unfractionated ester derivative prepared in Example 1, it was observed for dynamics of dropping into physiological saline similarly as above, revealing that it had a significantly longer period of time from the initiation of precipitation to the termination of solidification than that for the fractionated ester derivative.

The product obtained in this example, having a satisfactory ability of embolizing arteriovenous aneurysm, adequate viscosity and free-flowing ability, and easy handleability, will be quite advantageously used as an embolizing agent for embolizing arteriovenous aneurysm when used alone or in combination with a coil for embolizing arteriovenous aneurysm. If necessary, the product can be used by the addition of an adequate amount of an appropriate contrast medium for angiography suitable for the symptoms to be embolized.

EXAMPLE 4

Clinical Case

Using computed tomography (CT) and cerebral angiography, the head of a male patient, 35-year-old, who had been sent to the hospital after a sudden attack of headache and clouding of consciousness, was scanned and diagnosed as subarachnoid hemorrhage caused by the burst of an aneurysm, a size of 12 mm×12 mm, formed in the tip of a vertebral artery. A direct surgery was firstly planed as a treatment, however, since no penetrating blood vessel was found, an embolizing surgery using a platinum coil for embolizing arteriovenous aneurysm was conducted twice in place of the direct surgery, resulting in a substantially complete embolization of the aneurysm.

However, after a half year, radioscopy for intracranial arteries of the patient revealed that an interstice was formed within the cavity of aneurysm and the blood flow had been recirculated. Therefore, using an embolizing agent comprising an ester derivative of cellulose prepared by the method in Example 2, the patient was received with another emboliza-
tion surgery in accordance with the method mentioned above, resulting in a success of complete embolization throughout the interstice and the pedicel of the aneurysm. After additional two months later, radioscope for intracranial arteries of the patient revealed that there was no change in the embolized aneurysm. Neither postoperative serious neurological change nor dyskinesia in the patient was observed, and he was able to restart his work.

These results show that the ester derivatives of polysaccharides of the present invention are distinctively useful for embolizing arteriovenous aneurysm and that arteriovenous aneurysm will be more effectively embolized by using the embolizing agent of the present invention and conventional coils for embolizing arteriovenous aneurysm in combination. At present, the most commonly used means for embolizing arteriovenous aneurysm in intravascular surgeries are coils for embolizing arteriovenous aneurysm using metal coils such as platinum coils. However, in the use of using such coils, as exemplified in the above case, an interstice(s) may be formed within the cavity of aneurysm and the blood flow may recirculate as a result of changing in the shape of arteriovenous aneurysm treated with the coil or the shrink of the coil per se. When such coils and the embolizing agent of the present invention are used sequentially or in combination, the coils act as a "frame" and the ester derivative of a polysaccharide precipitates and solidifies in or around the coils. Thereby, a rigid, solid mass is formed in compliance with the shape of the arteriovenous aneurysm, which is not easily attained by either of them alone. As a result, interstices are scarcely formed within arteriovenous aneurysm after surgery, and both the risks of the blood flow recirculation and the burst of arteriovenous aneurysm are minimized.

INDUSTRIAL APPLICABILITY

As described above, the present invention was made based on the self-finding that ester derivatives of polysaccharides, having a specific weight-average molecular weight and a specific average substitution degree, are used as embolizing materials which are easily handleable and stable in quality. The embolizing agent for embolizing arteriovenous aneurysm, which comprises the ester derivative(s), exerts distinctive effect on the treatment and the prevention of hemorrhage, blood pressure reduction, thrombus, and inflammatory, which are accompanied by subarachnoid hemorrhage and arteriovenous aneurysm in general, by using alone or in combination with coils for embolizing arteriovenous aneurysm and applying to arteriovenous aneurysm occurred in parts which could not be easily received with a direct surgery, those with a failure of a direct surgery, those with a high risk of conducting surgeries in view of their size, site/region, neurotic symptom, or the like, and those of patients who could not endure general anesthesia. In addition, the embolizing agent of the present invention has a variety of uses as those which need the embolization of a relatively minute affected part, for example, hemostatics and hemostatic agents for interrupting the blood flow in medical fields; and reinforcing agents and fillers for cloths, papers, membranes, films, and sheets in the fields of clothes, papermaking, and chemicals.

The present invention with such outstanding functions and effects is a significantly useful invention that greatly contributes to this art.

The invention claimed is:

1. In a method for embolizing an arteriovenous aneurysm in a patient, the improvement comprising administering to said patient an ester derivative of a polysaccharide, wherein the polysaccharide is selected from the group consisting of pullulan and elsinan as an embolizing material, said ester derivative (i) having a weight-average molecular weight of 10,000 to 500,000 daltons, (ii) having a ratio of the weight-average molecular weight to the number average molecular weight of below two, (iii) having an average substitution degree of acyl group of greater than 2.5 (iv) being preparable into a solution with a viscosity of below 1,000 centipoises (cps) at 20° C. when dissolved in dimethyl sulfoxide; (v) being substantially insoluble in blood, and (vi) having a solubility in dimethyl sulfoxide of at least 10 mg/ml at 20° C.

2. An embolizing agent for arteriovenous aneurysm, comprising an embolizing material comprising (A) an ester derivative of a polysaccharide, wherein said polysaccharide is selected from the group consisting of pullulan and elsinan, (I) having a weight-average molecular weight of 10,000 to 500,000 daltons, (ii) having a ratio of the weight-average molecular weight to the number average molecular weight of below two, (iii) having an average substitution degree of acyl group of greater than 2.5, (iv) being preparable into a solution with a viscosity of below 1,000 centipoises (cps) at 20° C. when dissolved in dimthyl sulfoxide; (v) being substantially insoluble in blood, and (vi) having a solubility in dimethyl sulfoxide of at least 10 mg/ml at 20° C.

3. The embolizing agent of claim 2, wherein an ester derivative of a polysaccharide in said water-soluble organic solvent has a concentration of at least one percent by weight.

4. The embolizing agent of claim 2, further comprising an appropriate contrast medium for use in angiography.

5. The embolizing agent of claim 2, wherein said arteriovenous aneurysm is a cerebral aneurysm.

6. A method of producing an embolizing agent, which comprises dissolving an embolizing material in dimethyl sulfoxide to give a solution having concentration of 1 to 10% by weight and viscosity of below 1,000 centipoises (cps) at 20° C., and collecting the resulting solution, said embolizing material comprising an ester derivative of a polysaccharide, wherein said polysaccharide is selected from the group consisting of pullulan and elsinan, said ester derivative having a weight-average molecular weight of 10,000 to 500,000 daltons, a ratio of the weight-average molecular weight to the number average molecular weight of below two, and an average substitution degree of acyl group of greater than 2.5; said ester derivative being substantially insoluble in blood, having a solubility in dimethyl sulfoxide of at least 10 mg/ml at 20° C.

* * * * *

UNITED STATES PATENT AND TRADEMARK OFFICE
CERTIFICATE OF CORRECTION

| | | |
|---|---|---|
| PATENT NO. | : 7,414,038 B2 | Page 1 of 1 |
| APPLICATION NO. | : 10/148971 | |
| DATED | : August 19, 2008 | |
| INVENTOR(S) | : Kinugasa et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1309 days.

Signed and Sealed this
Thirtieth Day of October, 2012

David J. Kappos
*Director of the United States Patent and Trademark Office*